US009943557B2

(12) United States Patent
Lau

(10) Patent No.: US 9,943,557 B2
(45) Date of Patent: Apr. 17, 2018

(54) COMPOSITION COMPRISING OKRA FOR USE IN REDUCING DIETARY FAT ABSORPTION

(71) Applicant: INQPHARM GROUP SDN BHD, Kuala Lumpur (MY)

(72) Inventor: Kai Zhia Lau, Kuala Lumpur (MY)

(73) Assignee: INQPHARM GROUP SDN BHD, Kuala Lumpur (MY)

( * ) Notice: Subject to any disclaimer, the term of this patent is extended or adjusted under 35 U.S.C. 154(b) by 0 days.

(21) Appl. No.: 15/111,353

(22) PCT Filed: Jan. 16, 2015

(86) PCT No.: PCT/MY2015/000004
§ 371 (c)(1),
(2) Date: Jul. 13, 2016

(87) PCT Pub. No.: WO2015/108408
PCT Pub. Date: Jul. 23, 2015

(65) Prior Publication Data
US 2016/0331795 A1 Nov. 17, 2016

(30) Foreign Application Priority Data

Jan. 16, 2014 (MY) .......................... PI 2014700119

(51) Int. Cl.
| | |
|---|---|
| A61K 36/185 | (2006.01) |
| A23L 33/10 | (2016.01) |
| A23L 33/105 | (2016.01) |
| A23L 33/21 | (2016.01) |
| A23L 33/22 | (2016.01) |
| A23L 33/125 | (2016.01) |
| A61K 31/194 | (2006.01) |
| A61K 31/733 | (2006.01) |
| A23L 33/00 | (2016.01) |

(52) U.S. Cl.
CPC ............ *A61K 36/185* (2013.01); *A23L 33/10* (2016.08); *A23L 33/105* (2016.08); *A23L 33/125* (2016.08); *A23L 33/21* (2016.08); *A23L 33/22* (2016.08); *A23L 33/30* (2016.08); *A61K 31/194* (2013.01); *A61K 31/733* (2013.01); *A23V 2002/00* (2013.01)

(58) Field of Classification Search
CPC .......... A23V 2200/332; A23V 2250/21; A23V 2250/5062; A23L 33/105; A23L 33/10; A23L 33/21; A23L 33/22; A23L 33/30; A61K 31/194; A61K 31/733; A61K 36/185; A61K 9/10
See application file for complete search history.

(56) References Cited

U.S. PATENT DOCUMENTS 3,100,143 A * 8/1963 Doggett ................. A23B 7/022
34/331
5,851,963 A * 12/1998 O'Bryant ............. C10M 109/00
508/216
2013/0189411 A1* 7/2013 Henry ..................... A23L 1/217
426/321

FOREIGN PATENT DOCUMENTS

CN 103005261 A * 4/2013
WO 2010/010949 A1 1/2010

OTHER PUBLICATIONS

Gemede et al. (Journal of Food Processing and Technology, 2015, vol. 6, pp. 1-6).*
Han et al. (Journal of the Royal Society of Medicine Cardiovascular Disease, 2016, vol. 5, pp. 1-13).*
Sabitha et al (Journal of Pharmacy and BioAllied Sciences, 2011, vol. 3, pp. 397-402).*
Balkau et al. (1999) "Comment on the provisional report from the WHO consultation," Diabetic Medicine. 16(5):442-443.
Bercochea-Lopez et al. (2009) "Fungal chitin-glucan from Aspergillus niger efficiently reduces aortic fatty streak accumulation in the high-fat fed hamster, an animal model of nutritionally induced atherosclerosis," J. Agric. Food Chem. 57:1093-1098.
Daubioul et al. (2002) "Dietary Fructans, but not Cellulose, Decrease Triglyceride Accumulation in the Liver of Obese Zucker fa/fa Rats 1," Nutrient Interactions and Toxicity. 2002:967-973.
Delzenne et al. (2001) "Effects of fructans-type prebiotics on lipid metabolism," Am. J. Nutr. 73:456S-458S.
Fan et al. (Nov. 26, 2013) "Okra polysaccharide improves metabolic disorders in high-fat diet-induced obese C57BL/6 mice," Mol. Nutr. Food Res. 57(11):2075-2078.
Heck et al. (2000) "Orlistat, a new lipase inhibitor for the management of obesity," Pharmacotherapy. 20:270-279.
International Diabetes Federation (2006) "The IDF consensus worldwide definition of the Metabolic Syndrome," International Diabetes Federation.
Kahlon et al. (2007) "In vitro binding of bile acids by okra, beets, asparagus, eggplant, turnips, green beans, carrots, and cauliflower," Food Chem. 103(2):676-680.
National Institutes of Health (2001) "Third Report of the National Cholesterol Education Program (NCEP) Expert Panel on Detection Evaluation, and Treatment of High Blood Cholesterol in Adults (Adult Treatment Panel III): Executive Summary," NIH Publication No. 01-3670. National Institutes of Health.
Sabitha et al. (2011) "Antidiabetic and antihyperlipidemic potential of *Abelmoschus esculentus* (L.) Moench. in streptozotocin-induced diabetic rats," J. Pharm. Bioallied Sci. 3(3):397-402.
U.S. Food and Drug Administration (Aug. 24, 2009) "Early Communication about an Ongoing Safety Review Orlistat (marketed as Alli and Xenical)" Press Release. Accessible on the Internet at URL: http://www.fda.gov/Drugs/DrugSafety/PostmarketDrugSafety InformationforPatientsandProviders/DrugSafetyInformationfor HeathcareProfessionals/ucm179166.htm. [Last Accessed Sep. 1, 2016].

(Continued)

*Primary Examiner* — Mark V Stevens
(74) *Attorney, Agent, or Firm* — Lathrop Gage LLP; James H. Velema, Esq.

(57) ABSTRACT

Composition comprising (optionally processed) edible parts of an okra plant species for use in reducing dietary fat absorption in a subject or for use in treating or preventing obesity and/or for use in treating or preventing a metabolic disease such as metabolic syndrome, or for managing the weight of a subject, by binding dietary fat in the subject's stomach.

15 Claims, 3 Drawing Sheets

(56) References Cited

OTHER PUBLICATIONS

World Health Organization (1999) "Definition, Diagnosis and Classification of Diabetes Mellitus and its Complications. Part 1. Diagnosis and Classification of Diabetes Mellitus," Document No. WHO/NCD/NCS/99.2. World Health Organization.
International Search Report with Written Opinion corresponding to International Patent Application No. PCT/MY2015/000004, dated Jun. 2, 2015.

* cited by examiner

COMPOSITION COMPRISING OKRA FOR USE IN REDUCING DIETARY FAT ABSORPTION

RELATED APPLICATIONS

This application is a 35 U.S.C. § 371 filing of International Application No. PCT/MY2015/000004, filed Jan. 16, 2015, which claims priority to Malaysia Patent Application No. PI 2014700119, filed Jan. 16, 2014, each of which is incorporated herein by reference in their entireties.

TECHNICAL FIELD

The present invention is directed to compositions comprising edible parts of an okra plant species, optionally in combination with other active ingredients, for use in reducing dietary fat absorption. The compositions are particularly useful for treating or preventing obesity and/or for treating or preventing metabolic diseases, such as metabolic syndrome.

BACKGROUND OF THE INVENTION

Due to the increasing prevalence of obesity in the global population, body weight management has become a key element of modern healthcare, and more effective means of weight reduction are needed.

Obesity can result from a level of energy intake which exceeds the body's energy expenditure. Reduction of body weight may be achieved via reducing total caloric intake from the diet, or by reducing caloric intake contributed by specific dietary components. For example, caloric intake can be reduced by control of dietary fat consumption or via control of fat absorption in vivo. Because of its role in the pathogenesis of cardiovascular disease, control of fat intake is important.

Lifestyle changes can be difficult to implement, and as physical activity in the developed world continues to decline and Western-style diets are adopted by developing countries, the prevalence of obesity and its associated health problem is expected to increase worldwide. However, the effectiveness of currently available drugs and supplements for promoting weight control or weight loss is very variable, particularly if they are not used in conjunction with a calorie-restricted diet and exercise regimen.

Orlistat has been approved as an anti-obesity drug by the US Food and Drug Administration. Marketed under the names Xenical and Alli, Orlistat inhibits pancreatic lipase activity in the small intestine. Pancreatic lipase breaks down triglycerides into fatty acids and monoglycerides, which are subsequently absorbed into the body. Thus, inhibition of lipase activity effectively reduces fat absorption. A reduced fat diet is recommended while taking this medication. In the absence of a major dietary change, the adverse effects of gastrointestinal discomfort, diarrhea and flatulence have limited its use (See Heck et al, *Orlistat, a new lipase inhibitor for the management of obesity*, Pharmacotherapy, 20, p 270-279, 2000). There have also been reports of severe liver damage, including cases of liver failure, in patients taking this agent between 1999 and 2008 (US Food and Drug Administration press release 24 Aug. 2009). Another drug, Sibutramine, is a serotonin and norepinephrine reuptake inhibitor, and reduces body weight by suppressing appetite. However, a review by the European Medicines Agency found that the cardiovascular risks of Sibutramine outweigh its benefits. Emerging evidence suggests that there is an increased risk of non-fatal heart attacks and strokes with this medicine.

Because of the side effects of existing drugs such as those discussed above, there is an on-going need to develop new compositions to control body weight and/or treating obesity, and related disorders, such as metabolic syndrome.

SUMMARY OF THE INVENTION

According to a first aspect, there is provided a composition comprising edible parts of an okra plant species for use in reducing dietary fat absorption in a subject, for example, a human or an animal subject.

According to a second aspect, there is provided a composition for reducing dietary fat absorption, said composition comprising edible parts of an okra plant species, a fructan and an organic acid.

According to a third aspect, there is provided a composition comprising edible parts of an okra plant species, a fructan and an organic acid, for use in treating obesity in a subject.

According to a fourth aspect, there is provided a composition comprising edible parts of an okra plant species, a fructan and an organic acid, for use in treating a metabolic disease in a subject.

According to a fifth aspect, there is provided a method for reducing dietary fat absorption in a subject, said method comprising administering an effective amount of a composition comprising edible parts of an okra plant species to the subject such that dietary fat absorption is reduced, optionally wherein the composition further comprises a fructan and an organic acid.

According to a sixth aspect, there is provided a method for treating or preventing obesity in a subject, said method comprising administering an effective amount of a composition comprising edible parts of an okra plant species such that obesity is treated or prevented, optionally wherein the composition further comprises a fructan and an organic acid.

According to a seventh aspect, there is provided a method for treating or preventing a metabolic disease in a subject, said method comprising administering an effective amount of a composition comprising edible parts of an okra plant species such that said metabolic disease is treated or prevented, optionally wherein the composition further comprises a fructan and an organic acid.

According to an eighth aspect, there is provided a non-therapeutic method for managing the body weight of a subject, said method comprising administering an effective amount of a composition comprising edible parts of an okra plant species to the subject such that the subject's weight is managed, optionally wherein the composition further comprises a fructan and an organic acid.

According to a ninth aspect, there is provided the use of a composition comprising edible parts of an okra plant species for reducing dietary fat absorption in a subject.

According to a tenth aspect, there is provided the use of a composition comprising edible parts of an okra plant species for controlling, maintaining or reducing the body weight of a subject.

According to an eleventh aspect, there is provided a foodstuff, or a food supplement, or a dietary supplement, or a meal replacement product, or beverage, or beverage supplement comprising an effective amount of edible parts of an okra plant species, optionally wherein the effective amount is sufficient for managing the weight of a subject in accordance with the method of the eighth aspect of the present invention.

According to a twelfth aspect, there is provided a pharmaceutical composition comprising an effective amount of edible parts of an okra plant species and one or more pharmaceutically acceptable carriers, optionally wherein the effective amount is effective to treat or prevent obesity and/or a metabolic disease (e.g., metabolic syndrome) in a subject, optionally wherein the pharmaceutical composition further comprises a fructan and an organic acid.

DETAILED DESCRIPTION

Figure 1:
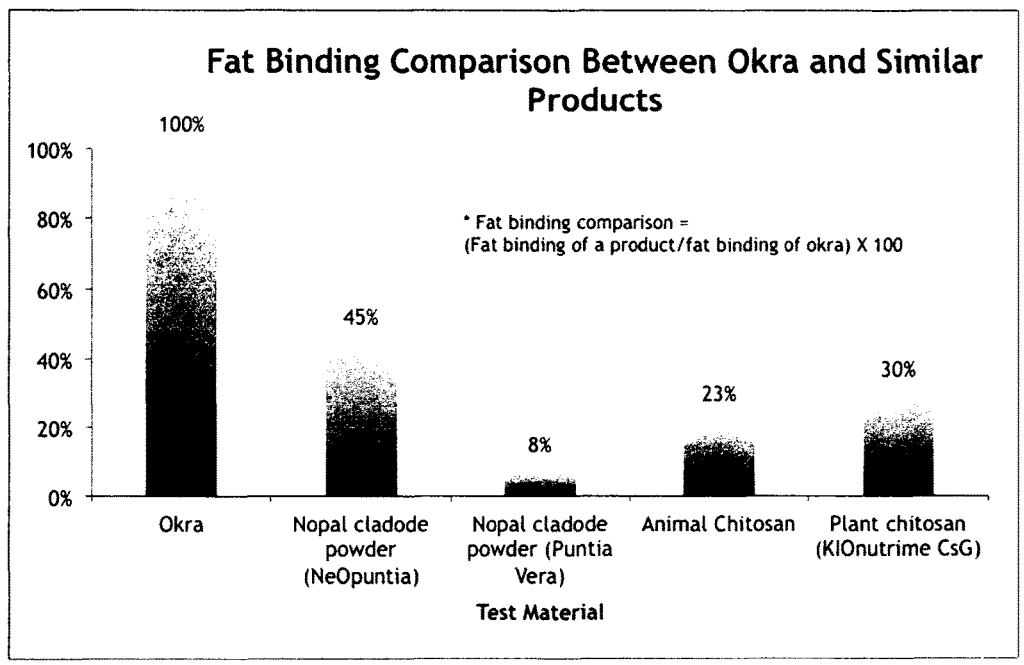
FIG. 1 is a graph comparing the fat binding capacity of an okra powder according to one of the embodiments of the invention with the natural products nopal and chitosan.

In certain embodiments, the okra plant species is an okra plant belonging to the genus *Abelmoschus*, more particularly, the species *Abelmoschus esculentus* (also sometimes referred to as *Hibiscus esculentus*), *Abelmoschus caillei* (also known as West African okra), *Abelmoschus manihot Abelmoschus ficulneus, Abelmoschus moschatus* or a mixture of any of the two or more species.

By "edible" is meant that the processed okra plant species is suitable for human or animal consumption, i.e., capable of being eaten. As such, the composition will comprise edible parts of the okra plant. In certain embodiments, the edible parts comprise the fruits (i.e., pods) of the okra plant. In such embodiments, the edible parts may or may not comprise okra seeds. In other embodiments, the edible parts are essentially free of okra seeds. By "essentially free" is meant that the edible parts comprise less than about 10% by weight okra seeds, based on the total weight of edible parts, for example, less than about 5% by weight okra seeds, or less than about 2% by weight okra seeds, or less than about 1% by weight okra seeds, or less than about 0.5 wt. % okra seeds, or less than about 0.1 wt. % okra seeds. In certain embodiments, the edible parts of the okra plant species and, thus, any composition comprising said edible parts, is entirely free of okra seeds.

In certain embodiments, the composition comprises processed edible parts of an okra plant species. By "processed" is meant that the okra plant has been modified by a process, e.g., by dehydrating or freeze drying, such that it is in a form suitable for incorporation in a composition according to the present invention. The okra plant may be modified by dehydrating (i.e., reducing moisture content) and/or sizing, advantageously, a combination of at least dehydrating and sizing. By "sizing" is meant that the (optionally dehydrated) edible parts of an okra plant are subjected to a particle size reduction step or steps. In certain embodiments, the edible parts of an okra plant are dehydrated and then sized. Processing may also comprise washing, blanching and/or cooking. Prior to dehydrating and/or sizing, the edible parts, e.g., pods (peeled or unpeeled) may be washed to remove dirt, and trimmed to remove discolored or damaged tissue. The pods may be sliced or otherwise chopped and the seeds may be removed. The pods are then dehydrated, for example, in a dryer or drying oven or by freeze drying, and the like, until the moisture content is below a desired level, for example, i.e., a moisture content of less than about 10%, for example, less than about 5%, or less than about 2%, or less than about 1%. The moisture content is determined by weight loss on drying, i.e., a moisture content of less than about 10% means that greater than about 90% of the moisture content of the okra plant species has been removed. A suitable loss on Drying' method is found in European Pharmacepeia (8th edition) section 2.2.32. The dehydrated product may then be crushed, ground, milled or otherwise pulverised, to produce a granular or powdered product. The crushed, ground, milled or otherwise pulverised product may be subjected to one or more classification steps so to obtain a granular or powdered product having a requisite particle size. The edible parts of an okra plant species may be provided in solid form or a non-solid form, e.g., as a liquid, for example, an aqueous liquid, or as a suspension or dispersion, for example, an aqueous suspension or dispersion.

In certain embodiments, the (optionally) processed okra plant species is used or included in the composition in a granular or powdered form. In certain embodiments, the edible parts of an okra plant species have a particle size diameter of less than about 750 µm, as may be determined by an appropriately sized sieve (e.g., a sieve having the appropriate US mesh size), for example, a particle size diameter of equal to or less than about 500 µm, or equal to or less than about 425 µm, or equal to or less than about 355 µm, or equal to or less than about 300 µm, or equal to or less than about 250 µm, or equal to or less than about 180 µm, or equal to or less than about 150 µm, or equal to or less than about 125 µm, or equal to or less than about 105 µm, or equal to or less than about 90 µm. Advantageously, the edible parts of an okra plant species have a particle size diameter of equal to or less than about 180 µm. In certain embodiments, the edible parts of an okra plant species has a particle size diameter of greater than about 1 nm, for example, greater than about 100 nm, or greater than about 1 µm, or greater than about 10 µm, or greater than about 37 µm, or greater than about 44 µm, or greater than about 53 µm. In certain embodiments, the edible parts of an okra plant species has a particle size diameter of equal to or less than about 500 µm to greater than about 37 µm, for example, equal to or less than about 300 µm to greater than about 53 µm, or equal to or less than about 250 µm to greater than about 53 µm, or equal to or less than about 180 µm to greater than about 53 µm, or equal to or less than about 150 µm to greater than about 53 µm, or equal to or less than about 125 µm to greater than about 53 µm, or equal to or less than about 150 µm to greater than about 90 µm, or equal to or less than about 125µ to greater than about 90 µm.

In certain embodiments, for example, embodiments in which a reduction in absorption of dietary fat occurs in the gastrointestinal tract (e.g., by binding of dietary fat in the stomach), the (optionally processed) edible parts of an okra plant species has a particle size diameter of equal to or less than about 150 µm, or equal to or less than about 125 µm, or equal to or less than about 90 µm. In certain embodiments, the edible parts of an okra plant species has a particle size diameter of equal to or less than about 180 µm to greater than about 150 µm, or equal to or less than about 150 µm to greater than about 125 µm, or equal to or less than about 125 µm to greater than about 90 µm.

The expression "absorption of dietary fat" and analogous terms used herein refers to the process by which the products of digestion of fats present in the diet pass through the gut mucosa into the blood or lymph. Dietary fat is predominantly triglyceride, and also includes phospholipids, sterols such as cholesterol, and fat-soluble vitamins and minerals. The small intestine also contains lipids from sloughed epithelial cells and cholesterol delivered in bile. In order for triglyceride to be absorbed, large aggregates of dietary triglyceride, which are virtually insoluble in an aqueous environment, must be broken down physically and held in suspension; this process is called emulsification. Triglyceride molecules must also be enzymatically digested by lipases yielding monoglyceride and fatty acids, which diffuse or are otherwise transported into the enterocytes.

The processed edible parts of the okra plant species comprise dietary fibre. The term "dietary fibre" used herein has its normal meaning for this term. It is generally regarded as the indigestible portion of food derived from plants. Typically, there are two main components of dietary fibre: soluble fibre, which dissolves in water, and insoluble fibre, which does not dissolve in water. In certain embodiments, the dietary fibre comprises polysaccharides, for example, non-starch polysaccharides, which are not degraded into absorbable units with the gastrointestinal tract. Thus, in certain embodiments, the dietary fibre comprises polysaccharides which cannot be hydrolysed by a mammalian, e.g., human, digestive system. It is believed that polysaccharides comprised within, and derived from, the (optionally processed) edible parts of an okra plant species, entrap or otherwise bind with dietary fat in the stomach, forming an indigestible polysaccharide-fat complex, which is excreted from the body as waste. The ability of the polysaccharide to complex with the dietary fat is due, at least in part, to the ability of the polysaccharide to swell in the small intestine. The overall effect is to reduce the body's ability to absorb dietary fat, which reduces calorie intake which, in-turn, can lead to weight loss and, thus, alleviation of disorders such as obesity and metabolic diseases such as metabolic syndrome, and any symptoms associated therewith. Thus, the composition comprising edible parts of an okra plant species reduces the absorption of dietary fat by binding with the dietary fat in the stomach such that the bound species cannot be digested by lipase in the stomach, is too large to be absorbed by the body, and is therefore excreted from the body as waste. Thus, advantageously, the composition comprising edible parts of an okra plant species acts on and binds with the dietary fat in the stomach before the dietary fat would otherwise be broken down and transported to the small intestine wherein it would normally be acted upon by bile acid during the digestion process.

The (optionally processed) edible parts of an okra plant species (having an activity for reducing dietary fat absorption) may be administered in the form of a composition comprising any suitable additional component. The composition may, for example, be a pharmaceutical composition (medicament), suitably for oral administration (e.g. tablet, capsule, powder, liquid, and the like). The composition may alternatively, for example, be a foodstuff, food supplement, dietary supplement, meal replacement product, beverage or beverage supplement.

The term "pharmaceutical composition" or "medicament" in the context of this invention means a composition comprising the (optionally processed) edible parts of an okra plant species and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of tablets, capsules, dragées, lozenges, granules, powders, pellets and cachets; liquid preparations including elixirs, syrups, suspensions, sprays, emulsions and solutions. Techniques and formulations generally may be found in Remington, The Science and Practice of Pharmacy, Mack Publishing Co., Easton, Pa., latest edition.

In solid dosage forms of the invention for oral administration, the active ingredient(s) may be mixed with one or more pharmaceutically acceptable carriers, such as dicalcium phosphate, and/or any of the following: diluents, fillers or extenders, such as starches, lactose, sucrose, glucose, mannitol, microcrystalline cellulose and/or silicic acid; binders, such as hydroxypropylcellulose, hydroxypropylmethylcellulose, carboxymethylcellulose, gelatine, polyvinyl pyrrolidones, polyvinyl acetate, sucrose and/or acacia; disintegrating agents, such as starch, for example, potato or tapioca starch, starch derivatives such as sodium starch glycoate, crospolyvinylpyrollidone, calcium carbonate, croscarmellose sodium, alginic acid, and certain silicates; lubricants, such as talc, calcium stearate, magnesium stearate, stearic acid, sodium sulphate sodium fumarate, solid polyethylene glycols; solubiliser such as sodium lauryl sulfate; flavouring and colouring agents; and mixtures thereof.

Tablets, and other solid dosage forms of the pharmaceutical compositions of the invention, may optionally be prepared with coatings and shells, such as enteric coatings and other coatings well known in the pharmaceutical-formulation art. They may also be formulated so as to provide slow or controlled release of the active ingredient(s) therein using, for example, natural and synthetic polymers such as hydroxypropylmethyl cellulose methacrylates, in varying proportions to provide the desired release profile; other polymer matrices, liposomes and/or microspheres may also be used. These compositions may also optionally contain colourants and/or opacifying agents and may be of a composition such that they release the active ingredient(s) only, or preferentially, in a certain portion of the gastrointestinal tract, optionally, in a delayed manner.

Liquid form preparations include solutions, suspensions, and emulsions, for example, water or water-propylene glycol solutions for oral administration. Liquid preparations can also be formulated in solution in aqueous polyethylene glycol solution. In certain embodiments, the active ingredient(s), i.e., including the processed edible parts of an okra plant species, may be mixed with one or more pharmaceutically acceptable carriers, such as water and/or any of the following: solvent such as propylene glycol, alcohol; humectant such as glycerol; sweeteners such as liquid glucose, corn syrup and sucrose; artificial sweeteners such as aspartame, stevia and sucralose; preservatives such as benzoates and parabens; viscosity modifiers/thickeners such as gums and alginates; buffering agents; flavouring agents and colouring agents.

Also included are solid form preparations which are intended to be converted, shortly before use, to liquid form preparations for oral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the solid form preparation as with a spoon, or other measuring device. The solid form preparations intended to be converted to liquid form may contain, in addition to the active material, flavourings, colourants, stabilizers, buffers, artificial and natural sweeteners, dispersants, thickeners, solubilising agents, and the like. The liquid utilized for preparing the liquid form preparation may be water, isotonic water, juices, milk, ethanol and the like as well as mixtures thereof.

The terms "food", "foodstuff", "food supplement", "dietary supplement", "health supplement", "meal replacement product", "beverage" and "beverage supplement" used herein have the normal meanings for those terms, and are not restricted to pharmaceutical preparations. Other composition forms are also included within the present invention. These may, for example, include, a foodstuff precursor such as a rehydratable powder or a beverage precursor such as a powder dispersible in water, milk or other liquid.

Also included are solid form preparations which are intended to be combined with a food or foodstuff before oral consumption. The solid form preparations may be mixed into the food or foodstuff or applied to the food or foodstuff, e.g., by sprinkling onto the food or foodstuff. Such solid forms include powders, granules, pellets and the like. Such food of foodstuffs include, without limitation, prepared meals (cooked or fresh), soup, dairy based products (e.g., yoghurt, cream, crème-freche), flour based products such as bread and pasta, snack or convenience items such as snack bars (e.g., chocolate bars), confectionery products, and the like.

In certain embodiments, the food or foodstuff, and the like, comprises from about 0.1 wt. % to about 50 wt. % of the composition of the invention described herein, based on the total weight of the food or foodstuff, for example, from about 0.1 wt. % to about 40 wt. %, or from about 0.1 wt. % to about 30 wt. %, or from about 0.1 wt. % to about 20 wt. %, or from about 0.1 wt. % to about 15 wt. %, or from about 0.1 wt. % to about 10 wt. %, or from about 0.1 wt. % to about 8 wt. %, or from about 0.1 wt. % to about 6 wt. %, or from about 0.1 wt. % to about 4 wt. %, or from about 0.1 wt. % to about 2 wt. % of the composition of the invention described herein. In certain embodiments, the food or foodstuff, and the like, comprise at least about 0.2 wt. % of the compositions of the invention described herein, based on the total weight of the food or foodstuff, for example, at least about 0.5 wt. %, or at least about 1 wt. %, or at least about 5 wt. % of the composition of the invention described herein.

In certain embodiments, the composition is orally administered daily to the subject. To achieve reduction in dietary fat absorption, the composition is to be taken in conjunction with meals that contain dietary fats. The composition is desirably administered with or after a meal, depending on the nature of the oral dosage form; for example, a capsule or tablet may be administered approximately 15 minutes to one hour after a meal, for example, 30 minutes to one hour after a meal, or 15 minutes to 30 minutes before or 30 minutes to 45 minutes after a meal.

The amount of composition administered may be varied depending upon the requirements of the subject and the amount of fat or fats in the food or diet being consumed. For therapeutic applications, the amount of composition administered may be varied depending upon the requirements of the subject, the severity of the condition being treated, and the amount of fat or fats in the food or diet being consumed.

Determination of the proper amount/dosage for a particular situation is within the skill of the art. For example, for therapeutic applications a physician or veterinarian having ordinary skill in the art can readily determine and prescribe the effective amount of the pharmaceutical composition required. The total daily amount/dosage may be divided and administered with meals in portions during the day if desired.

In general, a suitable daily dose of a composition according to the invention will be that amount of the composition which is the lowest dose effective to produce the desired effect, for example, a therapeutic effect, and/or to reduce dietary fat absorption. It is contemplated that a wide range of doses may be used, due to the non-toxic nature of the composition. For example, the dose may be up to 7.5 g per day. The dose amount pertains to the amount of processed edible parts of an okra plant species. In certain embodiments, the doses are in the range of 100 mg to about 7.5 g per day, which may be administered as two or three or more sub-doses administered separately at appropriate intervals (e.g., after each meal) throughout the day, optionally in unit dosage forms. In certain embodiments, the dose may be from about 200 mg to about 5 g per day, for example, from about 500 mg to about 3 g per day, or from about 750 to about 2 g per day, or from about 1000 mg to about 1750 mg per day, or from about 1000 mg to about 1500 mg per day. In certain embodiments, the composition may be administered two or three times a day, optionally with or after a meal. Thus, the dose may be at least about 100 mg per meal, or at least about 250 mg per meal, or at least about 500 mg per meal, or at least about 750 mg per meal, or from about 1000 per meal, or at least about 1250 mg per meal, or at least about 1500 mg per meal. In certain embodiments, the dose per meal is no more than about 2.5 g, for example, no more than about 2 g, for example, no more than about 1750 mg.

In certain embodiments in which the processed edible parts of an okra plant species is administered in the form of a composition, the amount of processed edible parts of an okra plant species comprises at least about 5% by weight of the composition, based on the total weight of the composition, for example, at least about 10% by weight, or at least about 15% by weight, or at least about 20% by weight, or at least about 25% by weight, or at least about 30% by weight or at least about 35% by weight, or at least about 40% by weight, or at least about 45% by weight, or at least about 50% by weight, or at least about 55% by weight, or at least about 60% by weight, or at least about 65% by weight, or at least about 70% by weight, or at least about 75% by weight, or at least about 80% by weight, or at least about 85% by weight, or at least about 90% by weight, or at least about 95% by weight or at least about 99% by weight. In certain embodiments, the composition comprises from about 1% to about 99% by weight of processed edible parts of an okra plant species, based on the total weight of the composition, for example, from about 5% to about 90% by weight, or from about 10% to about 80% by weight, or from about 10% to about 70% by weight, or from about 10% to about 60% by weight, or from about 15% to about 50% by weight, or from about 20% to about 50% by weight, or from about 20% to about 40% by weight of processed edible parts of an okra plant species.

In embodiments in which the edible parts of an okra plant species are incorporated in a composition for administration, the composition may comprise an additional source of dietary fibre, i.e., dietary fibre other than that derived from the okra plant species and/or dietary fibre other than a fructan, as described herein. The additional source of dietary fibre may comprise insoluble fibres, or soluble fibres, or a mixture of insoluble and soluble fibres.

In certain embodiments, the composition comprises: one or more soluble fibres selected from the group consisting of chitosan, gum acacia, guar gum, low-methoxy and high-methoxy pectin, oat and/or barley beta glucans, carrageenan, psyllium, cyclodextrin, and derivatives thereof; and/or one or more insoluble fibres selected from the group consisting of oat hull fibre, pea hull fibre, soy hull fibre, soy cotyledon fibre, sugar beet fibre, cellulose, corn bran and derivatives thereof.

In certain embodiments, the composition comprises chitosan and optionally one or more of the soluble and/or insoluble fibres described immediately above. Chitosan is a linear polysaccharide composed of randomly distributed β-(1-4)-linked D-glucosamine (deacetylated unit) and N-acetyl-D-glucosamine (acetylated unit). It may be manufactured by treating shrimp and other crustacean shells with an alkali, such as sodium hydroxide. Additionally or alternatively, Chitosan may be manufacture from fungal chitin (see, for example, Berecochea-Lopez et al., *J. Agric., Food Chem.*, 2009, 57, p 1093-1098).

In certain embodiments, the composition may comprises from about 0.1 to about 90% by weight of an additional source of dietary fibre, for example, from about 1% to about 80% by weight, or from about 5% to about 70% by weight, or from about 10% to about 60%, by weight, or from about 20% to about 50% by weight by weight of an additional source of dietary fibre, bases on the total weight of the composition.

In certain embodiments, the composition further comprises a fructan and an organic acid, such as a tricarboxylic acid. In certain embodiments, the fructan is inulin and/or sinistrin. Preferably, the fructan is inulin. Inulin is a naturally occurring polysaccharide produced by many types of plants, for example, from chicory. A characteristic of inulin is that fructosyl resides within the polysaccharide are linked by β-2,1 linkages. In certain embodiments, the organic acid is a tricarboxylic acid, malic acid, fumaric acid, tartaric acid, lactic acid, ascorbic acid or mixtures thereof. Suitable tricarboxylic acids may be selected from citric acid, isocitric acid, aconitic acid, carballylic acid and mixtures thereof. In certain embodiments, the tricarboxylic acid is citric acid. Advantageously, the composition further comprises inulin and citric acid. In certain embodiments, the composition comprises from about 0.5 wt. % to about 50 wt. % of a fructan (e.g., inulin) and from about 0.5 wt. % to about 20 wt. % wt. % of a an organic acid (e.g., a tricarboxylic acid, such as citric acid). In certain embodiments, the composition comprises from about 5 wt. % to about 45 wt. % of fructan (e.g., inulin) and from about 1 wt. % to about 15 wt. % organic acid (e.g., a tricarboxylic acid, such as citric acid), or from about 15 wt. % to about 40 wt. % of fructan (e.g., inulin) and from about 5 wt. % to about 15 wt. % organic acid (e.g., a tricarboxylic acid, such as citric acid), or from about 25 wt. % to about 40 wt. % of fructan (e.g., inulin) and from about 7 wt. % to about 12 wt. % organic acid (e.g., a tricarboxylic acid, such as citric acid), or from about 25 wt. % to about 35 wt. % of fructan and from about 8 wt. % to about 10 wt. % organic acid (e.g., a tricarboxylic acid, such as citric acid).

In certain embodiments, the composition of the present invention, including compositions of the invention which comprise fructan and organic acid, comprises a nutrient ingredient selected from the group consisting of vitamins and minerals, and combinations thereof. The vitamin may be any one or more of vitamin A, vitamin D, vitamin E, vitamin K, thiamine, riboflavin, pyridoxine, vitamin B12, carotenoids (including beta-carotene, zeaxanthin, lutein and lycopene), niacin, folic acid, pantothenic acid, biotin, vitamin C, choline, inositol, and salts and derivatives thereof. The mineral may be any one or more of calcium, phosphorous, magnesium, iron, zinc, manganese, copper, cobalt, boron, iodine, sodium, potassium, molybdenum, selenium, chromium, fluorine and chloride. If present, in certain embodiments, the composition comprises from about 0.001% to about 50% by weight of vitamin(s) and/or mineral(s), based on the total weight of the composition, for example, from about 0.5% to about 40% by weight, or from about 0.5% to about 30% by weight, or from about 0.5% to about 20% by weight, or from about 0.5% to about 10% by weight, or from about 0.5% to about 5%, or from about 0.5% to about 3%, or from about 0.1% to about 2%, or from about 0.1 to about 1% of vitamin(s) and/or mineral(s), based on the total weight of the composition. In certain embodiments, the composition comprises from about 0.001% to about 5 wt. %, for example, from about 0.001 to about 2 wt. %, or from about 0.001 to about 1 wt. %, or from about 0.001 to about 0.5 wt. %, or from about 0.001 to about 0.1 wt. %, or from about 0.001 to about 0.01 wt. % by weight of vitamin(s) and/or mineral(s), based on the total weight of the composition.

In certain embodiments, the composition of the present invention comprises other biologically active agents, for example, biologically active agents suitable for treating obesity and/or metabolic diseases such as metabolic syndrome. In certain embodiments, the biologically active agent is selected from the group consisting of absorption-altering agents, including lipase inhibitors e.g. orlistat and cetilistat, fat binders e.g. dehydrated *Opuntia ficus* indica cladode powder and chitosan, alpha-amylase inhibitors e.g. white kidney bean extract and polyphenols, alpha-glucosidase inhibitors e.g. acarbose, L-arabinose and polyphenols; appetite-altering agents, including pharmaceutical agents e.g. sibutramine, phentermine, diethylpropion, rimonabant and benzphetamine, and nutraceutical agents e.g. potato extract and protein; metabolism-altering agents e.g. moxonidine, green tea extract, *Citrus aurantium* extract or *Garcinia cambogia* extract; cholesterol-lowering agents, including statins e.g. atorvastatin, simvastatin, lovastatin, pravastatin, rosuvastatin etc, fibrates e.g. gemfibrozil, bezafibrate, fenofibrate or ciprofibrate, bile acid sequestrants e.g. colestipol, cholestyramine nutraceuticals e.g. plant sterol or any combination thereof. In certain embodiments, the biologically active agent or agents are present in the composition in an amount ranging from about 0.001 wt. % to about 20 wt. %, based on the total weight of the composition, for example, about 0.1 wt. % to about 15 wt. %, or from about 0.5 wt. % to about 10 wt. %, or from about 0.5 wt. % to about 5 wt. %, or from about 0.1 wt. % to about 3 wt. %, or from about 0.1 wt. % to about 2 wt. %, or from about 0.1 wt. % to about 1 wt. %, or from about 0.001 wt. % to about 5 wt. %, or from about 0.001 wt. % to about 2 wt. %, or from about 0.001 wt. % to about 1 wt. %, or from about 0.001 wt. % to about 0.5 wt. %, or from about 0.001 wt. % to about 0.1 wt. %, or from about 0.001 wt. % to about 0.01 wt. %.

The compositions of the present invention may be prepared by combining the processed edible parts of an okra plant species with one or more of the other ingredients described herein, i.e., fructan and organic acid (e.g., tricarboxylic acid), an additional source of dietary fibre, and/or vitamin(s), and/or minerals, and/or other biologically active agents, in suitable amounts to obtain a composition having the desired quantity of each component.

In certain embodiments, a mixture of the (optionally processed) edible parts of an okra plant species and any one or more of the additional ingredients described herein is prepared by mixing the (optionally processed) edible parts of an okra plant species and any one or more of the additional ingredients described herein. Such methods are well known in the art, for example, methods known in the food industry, such as those used in the preparation of health food bars and the like. This process may further comprise a forming step, wherein the mixture is moulded, pressed, spray dried or otherwise formed into a shape, e.g., a bar, ball, pellet or clusters (e.g., clusters of the type found in breakfast cereals, and the like), preferably with dimensions suitable for oral consumption by a human or other mammalian animal of the types described herein.

In certain embodiments, the composition of (optionally processed) edible parts of an okra plant species can be prepared by a method comprising:
 (a) washing;
 (b) slicing;
 (c) drying in an optimised temperature and humidity; and
 (d) milling to reduce the particle size of the dried mixture to obtain the powdered form.

Optionally, the powdered form of okra can be mixed with one or more of the additional ingredients described herein to obtain a composition with the (optionally processed) edible parts of an okra plant species with one or more of the additional ingredients.

Alternatively, the composition can be prepared by a method comprising:
 (a) mixing (optionally processed) edible parts of an okra plant species with one or more of the additional ingredients described herein;
 (b) adding water;
 (c) subjecting the wet mixture to a shear force, optionally at ambient temperature, to homogenize the mixture;
 (d) drying the homogenised mixture to reduce the water content, for example, to reduce the water content to 5 wt. % or below, and optionally
 (e) reducing the particle size of the dried mixture.

In certain embodiments, the shear force in step (c) may be suitably be applied by a high shear mixer. Other suitable means include blenders and twin-screw kneaders, which may be of a bench, laboratory or industrial scale. The particle size reduction step or steps may be carried out by means of milling, grinding or sieving, or a combination of such processes. Sieving will be carried out with a suitably sized mesh screen. The process may further comprise a forming step, wherein the (optionally particle size-reduced) mixture is moulded, pressed, spray dried or otherwise formed into a shape, e.g., a bar, ball, pellet or clusters (e.g., clusters of the type found in breakfast cereals, and the like), preferably with dimensions suitable for oral consumption by a human or other mammalian animal of the types described herein.

In other embodiments, a simple mixture of the (optionally processed) edible parts of an okra plant species and one or more of the additional ingredients described herein may be prepared by mixing methods well know in the art, for example, methods known in the food industry, such as those used in the preparation of health food bars and the like. As described above, this process may further comprise a forming step, wherein the mixture is moulded or pressed or otherwise formed into a shape, e.g., a bar, ball, pellet or clusters (e.g., clusters of the type found in breakfast cereals, and the like), preferably with dimensions suitable for oral consumption by a human or other mammalian animal of the types described herein.

In certain embodiments of the preparative methods described above, the method further comprises preparing the processed edible parts of an okra plant species in which okra fruits (pods) are modified by a combination of at least dehydrating and, where appropriate, sizing, as described herein above.

Besides being useful for human applications and treatments, the present invention is also useful in a range of mammals, which can also be affected by obesity and weight gain. Such mammals include non-human primates (e.g. apes, monkeys and lemurs), for example in zoos, companion animals such as cats or dogs, working and sporting animals such as dogs, horses and ponies, farm animals, for example pigs, sheep, goats, deer, oxen and cattle, and laboratory animals such as rodents (e.g. rabbits, rats, mice, hamsters, gerbils or guinea pigs).

In certain embodiments, the composition comprising edible parts of an okra plant species, a fructan and an organic acid, such as tricarboxylic acid (e.g., inulin and citric acid), is used in a method of treating or preventing obesity in a subject. In certain embodiments, the subject has not developed obesity, or has not been diagnosed as suffering from obesity, but is susceptible to obesity. The treatment or prevention of obesity is based on the ability of the composition comprising edible parts of an okra plant species to reduce the absorption of dietary fat, predominantly or exclusively in the gastrointestinal tract of a subject. As discussed above, this is based on the finding that the composition comprising edible parts of okra plant species binds dietary fat in the stomach, thereby reducing or even preventing the body from absorbing the dietary fat.

In certain embodiments, the composition comprising edible parts of an okra plant species, a fructan and an organic acid, such as tricarboxylic acid (e.g., inulin and citric acid), is used in a method of treating or preventing a metabolic disease (e.g., metabolic syndrome) in a subject. In certain embodiments, the subject has not developed a metabolic disease, e.g., has not developed metabolic syndrome, or has not been diagnosed as suffering from a metabolic disease (e.g., metabolic syndrome), but is susceptible to a metabolic disease (e.g., metabolic syndrome).

The expression "treating or preventing" and analogous terms used herein refers to all forms of healthcare intended to remove or avoid the disorder or to relieve its symptoms, including preventive and curative care, as judged according to any of the tests available according to the prevailing medical practice. An intervention that aims with reasonable expectation to achieve a particular result but does not always do so is included within the expression "treating or preventing". An intervention that succeeds in slowing or halting progression of a disorder is included within the expression "treating or preventing".

The expression "susceptible to" and analogous terms used herein refers particularly to individuals at a higher than normal risk of developing obesity and/or metabolic syndrome, as assessed using the known risk factors for the individual or obesity/metabolic syndrome. Such individuals may, for example, be categorised as having a substantial risk of developing obesity and/or metabolic syndrome, to the extent that medication would be prescribed and/or special dietary, lifestyle or similar recommendations would be made to that individual.

In certain embodiments, the subject is a human. In other embodiments, the subject is a mammal other than a human which can also be affected by obesity and weight gain, as described above.

Obesity is a medical condition in which excess body fat has accumulated to the extent that it may have an adverse effect on health, leading to reduced life expectancy and/or increased health problems. Subjects are considered obese when their body mass index (BMI), a measurement obtained by dividing a person's weight in kilograms by the square of the person's height in meters, exceeds 30 kg/m².

Obesity increases the likelihood of various diseases, particularly heart disease, type 2 diabetes, obstructive sleep apnea, certain types of cancer, and osteoarthritis.

BMI is calculated by dividing the subject's mass by the square of his or her height, typically expressed either in metric units:

$$BMI=\text{weight in kilograms}/(\text{height in meters})^2$$

The most commonly used definitions, established by the World Health Organization (WHO) in 1997 and published in 2000, provide the values listed in the table below.

| BMI | Classification |
|---|---|
| <18.5 | underweight |
| 18.5-24.9 | normal weight |
| 25.0-29.9 | overweight |
| 30.0-34.9 | class I obesity |
| 35.0-39.9 | class II obesity |
| ≥40.0 | class III obesity |

Metabolic syndrome is a combination of medical disorders that, when occurring together, increase the risk of a subject developing diseases such as cardiovascular disease and diabetes. Metabolic syndrome is also known as metabolic syndrome X, cardiometabolic syndrome, syndrome X, insulin resistance syndrome, Reaven's syndrome (named for Gerald Reaven), and CHAOS (in Australia).

There are a number of different definitions for metabolic syndrome, as follows:

The International Diabetes Federation consensus worldwide definition of metabolic syndrome (2006) is: central obesity (defined as waist circumference with ethnicity-specific values) and any two of the following:
- raised triglycerides: >150 mg/dL (1.7 mmol/L), or specific treatment for this lipid abnormality
- reduced HDL cholesterol: <40 mg/dL (1.03 mmol/L) in males, <50 mg/dL (1.29 mmol/L) in females, or specific treatment for this lipid abnormality
- raised blood pressure (BP): systolic BP >130 or diastolic BP >85 mm Hg, or treatment of previously diagnosed hypertension
- raised fasting plasma glucose (FPG): >100 mg/dL (5.6 mmol/L), or previously diagnosed type 2 diabetes
- If a subject's BMI is greater than 30 kg/m², central obesity can be assumed and waist circumference does not need to be measured.

The World Health Organization criteria (1999) require the presence of any one of diabetes mellitus, impaired glucose tolerance, impaired fasting glucose or insulin resistance, and two of the following:
- blood pressure: ≥140/90 mm Hg
- dyslipidemia: triglycerides (TG): ≤1.695 mmol/L and high-density lipoprotein cholesterol (HDL-C) 0.9 mmol/L (male), ≤1.0 mmol/L (female)
- central obesity: waist:hip ratio >0.90 (male); >0.85 (female), or body mass index >30 kg/m²
- microalbuminuria: urinary albumin excretion ratio ≤20 μg/min or albumin:creatinine ratio ≤30 mg/g The European Group for the Study of Insulin Resistance (1999) requires insulin resistance defined as the top 25% of the fasting insulin values among nondiabetic individuals and any two or more of the following:
- central obesity: waist circumference 94 cm (male), 80 cm (female)
- dyslipidemia: TG 2.0 mmol/L and/or HDL-C <1.0 mmol/L or treated for dyslipidemia
- hypertension: blood pressure 0.140/90 mmHg or antihypertensive medication
- fasting plasma glucose 6.1 mmol/L The US National Cholesterol Education Program Adult Treatment Panel III (2001) requires at least three of the following:
- central obesity: waist circumference ≥102 cm or 40 inches (male), ≥0.88 cm or 36 inches (female)
- dyslipidemia: TG ≥0.1.7 mmol/L (150 mg/dl)
- dyslipidemia: HDL-C <40 mg/dL (male), <50 mg/dL (female)
- blood pressure ≥130/85 mm Hg, or treated for hypertension
- fasting plasma glucose ≥6.1 mmol/L (110 mg/dl)

In certain embodiments, metabolic syndrome is as defined according to the International Diabetes Federation consensus worldwide definition of metabolic syndrome (2006).

In certain embodiments, metabolic syndrome is as defined according to The World Health Organization criteria (1999).

In certain embodiments, metabolic syndrome is as defined according to The European Group for the Study of Insulin Resistance (1999).

In certain embodiments, metabolic syndrome is as defined according to The US National Cholesterol Education Program Adult Treatment Panel III (2001).

In accordance with the therapeutic methods and applications of the present invention described herein, the composition comprising (optionally processed) edible parts of an okra plant species is administered in an effective amount such that obesity and/or a metabolic disease (e.g., metabolic syndrome) is treated or prevented. An effective amount will be understood to be an amount which is effective to treat or prevent obesity and/or a metabolic disease (e.g., metabolic syndrome), i.e., to produce a therapeutic effect. An effective amount includes any of the doses, dosages or dosage regimens described above, each of which pertains to the amount of the (optionally processed) edible parts of an okra plant species and, in certain embodiments, the amount of fructan (e.g., inulin) and an organic acid such as a tricarboxylic acid (e.g., citric acid). Unexpectedly, it has been found that the combination of edible parts of an okra plant species, a fructan (preferably inulin) and an organic acid such as a tricarboxylic acid (preferably citric acid) provides a synergistic improvement in the dietary fat absorption capacity of the composition compared to the dietary fat absorption capacity of each species alone. This means the dietary fat absorption properties of edible parts of an okra plant species can be enhanced. This, in turn, means that in principle less of the okra can be used to obtain the same effect.

The composition comprising (optionally processed) edible parts of an okra plant species, as described herein, may be used in a method of managing the weight of a subject. Such methods are essentially non-therapeutic in that they do not alleviate or treat a treatable disorder, but rather enable a subject to maintain a healthy weight (e.g., a BMI of from 18.5-24.9), or enable an overweight subject (e.g., a subject who has a BMI of from 25.0-29.9) to reduce their weight (i.e., reduce their BMI), preferably to a healthy weight, or to otherwise to reduce, minimize, ameliorate or prevent weight gain in a subject.

In general, a suitable daily dose of composition comprising (optionally processed) edible parts of an okra plant species will be that amount of the composition which is the lowest dose effective to produce the desired degree or type of weight management. In certain embodiments, the doses, dosages and dosage regimens described above will be suitable for the method of managing the weight of a subject. A person of ordinary skill in the art will understand that a suitable dose or dosage will typically vary from subject to subject, and will dependent on factors such as the dietary habits and severity of health conditions of the subject at the outset of administration of the composition comprising (optionally processed) edible parts of an okra plant species. For example, a subject seeking to maintain a healthy weight may need to consume a lesser amount of the composition comprising (optionally processed) edible parts of an okra plant species than an overweight subject seeking to reduce their weight. A subject on a high fat diet may need to consume a higher dose of the composition comprising (optionally processed) edible parts of an okra plant species. The method of managing weight may be combined with other conventional weight loss measures, such as, for example, an increase in physical activity and/or a healthy or healthier diet.

The invention will now be described in detail by way of reference only to the following non-limiting examples.

EXAMPLES

Example 1 Fat Binding Test—Methodology, Materials and Apparatus

The fat-binding efficacy of okra powder (see Test method in (d)) was determined in accordance with the procedures described below. The fat-binding efficacy of a number of known products (see Comparative Examples A, B, C and D) was tested in the same way and compared to the fat-binding efficacy of the okra powder. The test is a predictor of dietary fat absorption in vivo in the gastrointestinal tract (i.e., in the substantial absence of bile salts).
(a) Materials and Apparatus
  Analytical grade sunflower oil (Sigma)
  Trizma base, purity ≥9% (Sigma)
  37% HCl
  Centrifuge (angle rotor)
  Water bath
(b) Buffer Preparation
  pH 6.8 buffer:
    add 120 g of Trizma base into a beaker
    add 49.0 ml of HCl 37% (or equivalent to 12M HCl) into beaker
    top up with water to 200 ml
    adjust the pH to 6.8 with HCl 37%
(c) Okra Powder Preparation
  Okra pods were sliced and dried in an oven at 55-85° C. to reduce the moisture content to less than 10%. The dried material was then ground to a powder and passed through a 125 μm (120 US mesh) sieve. The material passing through the 125 μm sieve was used in the Examples.
(d) Test Method
  25 ml of a pH 2 buffer was added to a centrifuge tube. 12.0 g of a Sudan (III) red saturated sunflower oil preparation was then added followed by 0.30 g of the okra powder. The tube was agitated vigorously and incubated at 37° C. for 2 hours.

Following incubation, 5 ml of the pH 6.8 buffer was added to the centrifuge tube, which was closed tightly with cap. The contents were mixed gently. The tube was then centrifuged for 10 minutes.

Using a micropipette the, sunflower oil was recovered from the centrifuge and weighed.

The fat binding capacity of the okra powder was calculated as the ratio between the mass of sunflower oil unrecovered and the mass of okra powder used during the experiment, i.e., Fat binding capacity=(mass of sunflower oil used (g)−mass of sunflower oil recovered)/mass of okra powder.

Comparative Example A

The procedure in Example 1 was followed except that 0.3 g of nopal cladode powder, NeOpuntia® (manufactured by Nexira Health) was used instead of okra powder. The nopal cladode powder was passed through a 125 μm sieve prior to testing.

Comparative Example B

The procedure in Example 1 was followed except that 0.3 g of nopal cladode powder, Puntia Vera® (manufactured by Garuda International was used instead of okra powder. The nopal cladode powder was passed through a 125 μm sieve prior to testing.

Comparative Example C

The procedure in Example 1 was followed except that 0.3 g of food grade (animal) chitosan powder having a degree of acetylation (DAC) of 85% (manufactured by RongCheng LuYang Biological Technology Co., Ltd.) was used instead of okra powder. The animal chitosan powder was passed through a 125 μm sieve prior to testing.

Comparative Example D

The procedure in Example 1 was followed except that that 0.3 g of food grade plant chitosan, KIOnutrime-CsG® (manufactured by KitoZyme S.A) was used instead of okra powder. The plant chitosan was passed through a 125 μm sieve prior to testing.
(e) Results
  The tested okra powder was determined to have a fat binding capacity of 40 g fat/g of okra powder.

The fat binding capacity of the okra powder was compared to the fat binding capacity of the species tested in Comparative Examples A, B, C and D. The comparison is summarized in FIG. 1.

The fat binding comparison=(fact binding capacity of comparative example/fat binding capacity of okra)×100.

Example 2 Fat Absorption Capacity

The okra powder, nopal cladode powder (NeOpuntia®), animal chitosan powder and plant chitosan powder from Example 1 were further tested for fat absorption capacity. The fat absorption capacity of inulin and citric acid was also tested, as were combinations of the aforementioned powders with (i) inulin, (ii) citric acid, (iii) inulin and citric acid.

The fat absorption capacity was calculated as follows:

Fat absorption capacity=[(amount of sunflower oil used−amount of sunflower recovered)/amount of oil used]×100%.

For test samples comprising okra powder, nopal cladode powder (NeOpuntia®), animal chitosan powder or plant chitosan powder, 0.1 g of each powder was mixed with 20 g of sunflower oil. The mixture was then centrifuged for 10 mins at 6400 rcf. The fat absorption capacity for each test sample was then calculated.

For test samples comprising powder and inulin, 0.15 g of inulin was included.

For test samples comprising powder, inulin and citric acid, 0.15 g of inulin was included and 0.05 g of citric acid was included.

For test samples comprising inulin only, 0.600 g of inulin was mixed with 20 g of sunflower oil. For test samples comprising citric only, 0.600 g of citric acid was mixed with 20 g of sunflower oil. For test samples comprising inulin and citric acid only, 0.150 g of inulin and 0.050 g of citric acid was mixed with 20 g of sunflower oil.

Figure 2:
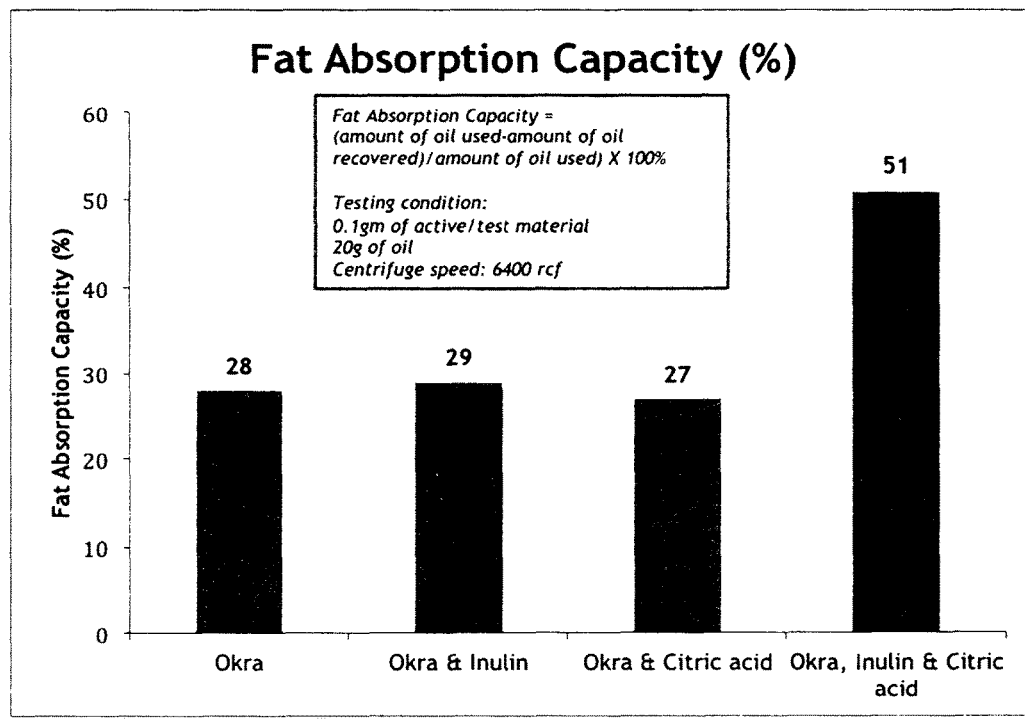
FIG. 2 is a graph comparing the fat binding capacity of a composition according to one of the embodiments of the invention comprising okra, inulin and citric acid with compositions which do not comprise all three components.
Figure 3:
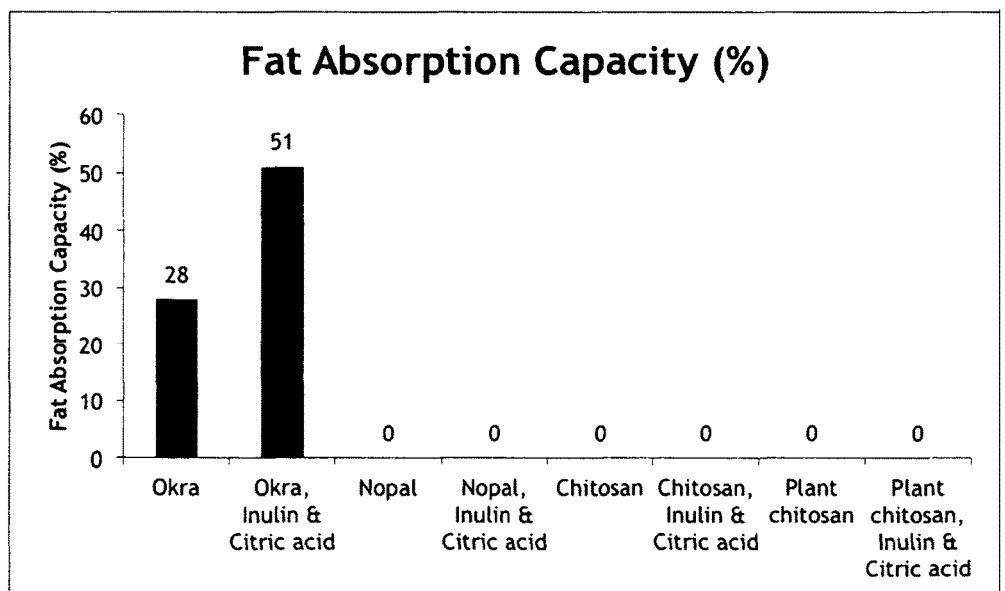
FIG. 3 is a graph comparing the fat binding capacity of a composition according to one of the embodiments of the invention comprising okra, inulin and citric with the natural products nopal and chitosan.

Results are summarized in FIGS. 2 and 3.

Example 3 Solid Dosage Formulation

Table 1 shows a composition of tablet formulation comprising okra alone and with addition of inulin and citric acid.

TABLE 1

| Ingredients Item | Formulation 1 | Formulation 2 |
|---|---|---|
| | Quantity per tablet (mg) | |
| 1. Okra | 500 | 650 |
| 2. Inulin | 100 | — |
| 3. Citric Acid | 100 | — |
| 4. Microcrystalline Cellulose | 114 | 164 |
| 5. Croscarmellose Sodium | 40 | 40 |
| 6. Silicon Dioxide | 10 | 10 |
| 7. Magnesium Stearate | 6 | 6 |
| 8. Hydroxypropyl methylcellulose coating | 30 | 30 |

Ingredients were dispensed according to the above formulation for a batch size of 2000 tablets. Item 1 was sieved through mesh size #100, while Item 2 to 5 were sieved through mesh #30. Item 1 was premixed with item 6 and blended for 2 minutes in a laboratory-scale drum blender. Item 2 to 5 were then added to the premixed and to be blended homogenously for 10 minutes. Item 7 was to be sieved through mesh #60 prior to lubrication with the blends for 2 minutes. The blend was compressed into oblong tablets at the weight of 870 mg. Compressed tablets were then coated with Item 8 until three percent of weight gain was achieved.

The invention claimed is:

1. A composition comprising edible parts of okra plant species, an added fructan and an added organic acid for reducing dietary fat absorption in a subject, wherein the okra plant species belongs to the genus *Abelmoschus*, wherein the edible parts of the okra plant species comprise fruit or pods in a granular or powdered form, the fructan is selected from the group consisting of inulin, sinistrin and combinations thereof, and the organic acid is selected from the group consisting of citric acid, aconitic acid, carballylic acid and combinations thereof, and wherein the composition is a pharmaceutical composition or dietary supplement in the form of an oral preparation.

2. A composition according to claim 1, wherein the composition comprises from about 20 wt. % to about 99 wt. % of the edible parts of an okra plant species, from about 0.5 wt. % to about 50 wt. % of inulin, and from about 0.5 wt. % to about 20 wt. % of organic acid, based on the total weight of the composition.

3. A composition according to claim 1, wherein the composition comprises polysaccharides derived from the okra plant species.

4. A composition according to claim 3, wherein the polysaccharides are non-starch polysaccharides, which are not degraded into absorbable units with the stomach or small intestine.

5. A composition according to claim 1, wherein the composition further comprises an additional source of dietary fibre other than that derived from the okra plant species.

6. A composition according to claim 5, wherein the composition comprises from about 20 wt. % to about 99 wt. % of the edible parts of an okra plant species, based on the total weight of the composition; from about 0.1 wt. % to about 90 wt. % of an additional source of dietary fibre other than that derived from the okra plant species, based on the total weight of the composition; and from about 0.001 wt. % to about 50 wt. % of one or more vitamins and/or minerals, based on the total weight of the composition.

7. A composition according to claim 1, wherein the okra plant species is *Abelmoschus esculentus, Abelmoschus caillei, Abelmoschus manihot, Abelmoschus ficulneus, Abelmoschus moschatus* or a mixture of any of the two or more species thereof.

8. A composition according to claim 1, wherein the edible parts of the okra plant species have a particle size diameter of less than about 180 μm.

9. A method for reducing dietary fat absorption in a subject, said method comprising administering an effective amount of a composition of claim 1.

10. A method for treating obesity in a subject, said method comprising administering an effective amount of a composition of claim 1.

11. A method for treating a metabolic disease in a subject, said method comprising administering an effective amount of a composition of claim 1.

12. A non-therapeutic method for managing the body weight of a subject, said method comprising administering an effective amount of a composition of claim 1.

13. A composition according to claim 1, further comprising one or more carriers and/or excipients.

14. A composition according to claim 1, wherein said fructan is inulin and said organic acid is citric acid.

15. The composition of claim 1, wherein the composition is in the form of a tablet, capsule, dragee, lozenge, pellet, cachet, elixir, syrup, suspension, spray, or emulsion.

* * * * *